United States Patent [19]

Kuragano et al.

[11] Patent Number: 4,987,252

[45] Date of Patent: Jan. 22, 1991

[54] QUENCHING PROCESS OF REACTION PRODUCT GAS CONTAINING METHACRYLIC ACID AND TREATMENT METHOD OF QUENCHED LIQUID

[75] Inventors: Morimasa Kuragano, Sakai; Kozo Iwasaki, Yokohama; Takeshi Isobe; Isao Fukada, both of Takaishi; Minoru Koshibe, Sakai; Yoshihiro Sezaki, Izumi; Hirozo Segawa; Katsuji Yoguchi, both of Kitakanbara, all of Japan

[73] Assignees: Mitsui Toatsu Chemicals, Incorporated; Kyowa Gas Chemical Industry Co., Ltd., both of Tokyo, Japan

[21] Appl. No.: 211,903

[22] Filed: Jun. 27, 1988

[30] Foreign Application Priority Data

| Jun. 27, 1987 | [JP] | Japan | 62-158825 |
| Jun. 27, 1987 | [JP] | Japan | 62-158827 |
| Aug. 5, 1987 | [JP] | Japan | 62-194345 |
| Aug. 5, 1987 | [JP] | Japan | 62-194346 |

[51] Int. Cl.$^5$ .................. C07C 57/07; C07C 57/075; C07C 51/50; C07C 47/22; C07C 45/86; C07C 45/81

[52] U.S. Cl. .................. 562/600; 562/485; 562/532; 562/538; 562/545; 568/459; 568/471; 568/476; 568/492

[58] Field of Search ............. 562/600, 545, 532, 538, 562/485; 568/492, 476, 459, 471

[56] References Cited

U.S. PATENT DOCUMENTS

4,554,054 11/1985 Coyle .................. 562/600

FOREIGN PATENT DOCUMENTS

| 9545 | 4/1980 | European Pat. Off. . |
| 56-122327 | 9/1981 | Japan . |
| 57-91944 | 6/1982 | Japan . |
| 58-52239 | 3/1983 | Japan .................. 562/600 |
| 2004886 | 4/1979 | United Kingdom . |

*Primary Examiner*—Vivian Garner
*Attorney, Agent, or Firm*—Oblon, Spivak, McClelland, Maier & Neustadt

[57] ABSTRACT

In order to recover methacrolein and/or methacrylic acid by quenching a reaction product gas obtained by catalytic oxidation of isobutylene or the like, the reaction product gas is charged into a quench column through a double-wall pipe and is then brought into contact with a condensate as a cooling medium. Deposition of terephthalic acid and the like inside the column is prevented by controlling the temperature of a bottom in the quench column and that of an overhead gas of a quench column unit. An aromatic carboxylic acid, aromatic aldehyde, metal powder is added to an aqueous solution of methacrylic acid, which contains terephthalic acid and the like, so that the terephthalic acid and the like are caused to precipitate for their removal.

4 Claims, 2 Drawing Sheets

QUENCHING PROCESS OF REACTION PRODUCT GAS CONTAINING METHACRYLIC ACID AND TREATMENT METHOD OF QUENCHED LIQUID

BACKGROUND OF THE INVENTION

(1) Field of the Invention

This invention relates to a process for quenching a reaction product gas, which has been obtained by subjecting isobutylene or the like to vapor-phase catalytic oxidation, so as to recover methacrolein and/or methacrylic acid, and in particular to a quenching process and also to a reasonable recovery process from the liquid thus quenched.

(2) Description of the Prior Art

A quench column is generally used for collecting methacrolein and/or methacrylic acid from a reaction product gas which has been obtained by subjecting at least one compound selected from isobutylene, tertiary butanol, isobutyl aldehyde and methacrolein to catalytic vapor-phase oxidation with molecular oxygen in the presence of steam in accordance with a one-step or two-step reaction. As the manner of gas-liquid contact in such a quench column, there are two methods, one being counter current contact and the other parallel flow contact. As liquid compounds usable for these contacts, may be mentioned a reaction-gas condensate, benzene, benzene derivatives substituted by one or more alkyl groups having 1–4 carbon atoms, alkoxyl groups and/or alkoxycarbonyl groups aliphatic hydrocarbons having 5–7 carbon atoms, alicyclic hydrocarbons, etc. The reaction product gas however contains, in addition to methacrolein and/or methacrylic acid as a target product, high boiling byproducts such as benzoic acid, toluic acid, maleic acid, citraconic acid, terephthalic acid and tar-like substances at rather high concentrations. A trouble may hence arise that these high boiling byproducts may precipitate in the course of cooling of the reaction product gas and could hence block pipe lines.

A variety of methods have therefore been proposed for the prevention of blocking of pipe lines, including by way of example (1) to maintain the reaction product gas at a temperature at least equal to the boiling point of maleic anhydride under the pressure of the reaction product gas and further to control the average linear velocity of the reaction product gas at 5 m/sec or higher (Japanese Patent Laid-Open No. 126605/1975), (2) to control the flow velocity of the reaction product gas at 10 m/sec or higher at its feeding port of a quench column and to bring the reaction product gas into parallel flow contact with a condensate (Japanese Patent Laid-Open No. 91944/1982), (3) to maintain the temperature of the reaction product gas at 130° C. or higher at the inlet of a scrubber (Japanese Patent Laid-Open No. 122327/1981), (4) to bring a gaseous reaction mixture into direct counter current contact at a temperature not higher than 100° C. with a portion of a condensate condensed and accumulated in advance (Japanese Patent Laid-Open No. 52027/1979), etc.

Although these methods are effective for the prevention of blocking of pipe lines as stated in their specifications, they cannot still be considered as fully effective methods. Namely, the use of these methods caused such a problem that a localized temperature drop occurred at an inlet of a quench column due to conduction of heat to surrounding elements of structure upon feeding the reaction product gas into the quench column or splashes of a condensate were concentrated at the tip of a gas flow-out portion to result in the deposition of high boiling byproducts when the condensate was fed as a parallel flow. Once the deposition of high boiling byproducts takes place as described above, the byproducts are impregnated with methacrolein and methacrylic acid contained in the reaction product gas. These compounds have poor thermal stability. They therefore undergo polymerization there and become thicker gradually, so that the pipe line is blocked.

It has been known to guide the reaction product gas to a collector, the temperature of which is maintained above the dew point of the gas but below 250° C., before condensing the gas (Japanese Patent Laid-Open No. 52239/1983), whereby high boiling byproducts are removed so as to improve such a drawback. In this method, high boiling and melting impurities contained in a gaseous form in the reaction product gas are forced to deposit for their removal However, the impurities thus deposited are composed of various substances. It is hence extremely difficult to remove the impurities completely within a similar temperature range. Many practical problems are also involved regarding the removal of the impurities thus precipitated and deposited.

The present inventors have already proposed to bring ammonia gas or ammonium hydroxide together with the condensate of the reaction product gas into contact with the reaction product gas so as to quench the reaction product gas (Japanese Patent Laid-Open No. 438/1987). This method is very effective in preventing the deposition of polybasic organic acids, e.g., terephthalic acid, as high boiling byproducts and also in preventing the polymerization of methacrolein and methacrylic acid. However, the ammonium salts of the above organic acids are partitioned to the side of an extraction residue in the subsequent extraction step and hence constitute a portion of an effluent. It is thus necessary to take a special measure for their treatment. Taking all the above features into consideration, the above method cannot be considered to be preferred fully.

It has also been attempted to solve the blocking of a pipe line by making improvements in equipment. In Japanese Patent Laid-Open No. 91944/1982 referred to above, the reaction product gas is introduced into a bottom portion of a quench column through a feed pipe provided at a right angle relative to a wall of the column, is blown against spreading buffle plates arranged in the form of a turned square U, and after being spread in horizontal directions, is allowed to flow upwards toward the top of the column. On the other hand, a portion of a condensate which has been cooled by a heat-exchanger is caused to fall as a shower along with a polymerization inhibitor from the top of the column, whereby the portion of the condensate is brought into counter current contact with the reaction product gas and the reaction product gas is hence quenched and condensed. In the above process, the cooled condensate which flows downwardly from the point above the spreading plates hits the spreading plates so that the spreading plates are cooled. The reaction product gas hence hits the spreading plates and is thus cooled, thereby resulting in condensation and coagulation of high boiling byproducts. Since the insides of the spreading plates are not exposed directly to the condensate containing the polymerization inhibitor, the condensation, coagulation and polymerization of the high boiling byproduct gas proceed at a tip portion of the feed pipe and the operation becomes no longer feasible eventually.

The above patent publication also discloses to introduce the reaction product gas and condensate from a top portion of a quench column, so that they are contacted to each other as parallel flows. In this method, the wall of the top portion is heated and due to conduction of heat, the lower wall is also exposed to high temperatures. The condensate supplied as the parallel flow splashes against the wall of the column The condensate is thus concentrated, leading to deposition of high boiling byproducts and polymerization of methacrolein and methacrylic acid.

In most of the above-described methods or processes for the quenching of the reaction product gas, it is proposed to condense the reaction product gas in a single step or multiple steps, generally at a temperature of 100° C. or lower. Very broad temperature ranges are only referred to. The polymerization of methacrylic acid and the like as well as the formation of a solid matter from terephthalic acid and the like are especially serious problems as described above. The former problem may generally be solved when the temperature is controlled as low as possible. The latter problem, especially, a solid matter spread and suspended in a vapor phase cannot however be removed by scrubbing in a conventional tray column or packed column. No sufficient technique has been known for the prevention of occurrence of such polymerization or solid formation. It is hence dominantly practiced to collect and remove solid matters, which are contained in a gas from a quenching step of the reaction product gas or a methacrolein absorption step, by means of a cyclon or a scrubber of the venturi type. Accordingly, a great deal of initial cost is required and moreover, there is a disadvantage that the reaction pressure must be increased to compensate a pressure loss by such an extra apparatus.

The reaction product gas quenched by the above method forms a vapor phase and a condensed liquid phase, and methacrylic acid is separated and purified in steps as will be described next. Namely, methacrolein as a useful component is absorbed and separated, usually, with an absorbent such as water or an organic solvent from the vapor phase containing nitrogen, oxygen, carbon monoxide, carbon dioxide and steam. On the other hand, from the liquid phase composed principally of methacrylic acid and containing small amounts of aldehydes such as methacrolein together with formic acid, acetic acid, propionic acid, acrylic acid and water, methacrolein as a useful component is stripped, separated and recovered along with the other aldehydes. When methacrolein is separated and recovered as described above, solid matters often deposit in a diffusion column, thereby developing an operational problem such as interior blocking of the column. Basically, solid matters such as terephthalic acid are only sparingly soluble in the aqueous solution of methacrylic acid. Due to their slow precipitation velocities, the aqueous solution is however fed to the diffusion column before such solid matters have precipitated fully. The solid matters hence occur in the diffusion column and deposit there.

After stripping, separating and recovering methacrolein together with other aldehydes in the above-described process, methacrylic acid is separated in a purified form usually by extracting the liquid phase with a solvent capable of extracting methacrylic acid selectively and then removing formic acid, acetic acid, propionic acid, acrylic acid and water, which are contained in small amounts in the extract, by azeotropic distillation with a solvent. In this selective extraction of methacrylic acid, solids matters often deposit in an extraction column to cause a problem for the stable operation of the process such as interior blocking of the column. Basically, solid matters led by terephthalic acid are only poorly soluble in the aqueous solution of methacrylic acid. Due to the low precipitation velocities of the solid matters, the aqueous solution is however fed to the extraction column before the solid matters have precipitated fully. The solid matters hence occur in the column and deposit there upon contact of the aqueous solution of methacrylic acid with the extracting solvent, although the degree of their deposition varies depending on the kind of the extracting solvent. As conventional techniques for solving these problems, it has been known to bring the aqueous solution into contact with the solvent before feeding the aqueous solution to the extraction column and then to filter off solid matters thus occurred (Japanese Patent Laid-Open No. 16438/1981), to add a basic substance to the aqueous solution before feeding the aqueous solution to the extraction column, thereby causing the solid matters to decompose or to move as salts to the side of an extraction residue (Japanese Patent Laid-Open No. 99434/1983), and to add a bisulfite to the aqueous solution before feeding the aqueous solution to the extraction column, thereby preventing the solid matters from occurring in the extraction column (Japanese Patent Laid-Open No. 128337/1983), etc. The above-described methods may be effective in removing organic compounds, such as terephthalic acid, dissolved in the aqueous solution of methacrylic acid in a stage prior to the extraction of methacrylic acid. However, large facilities are required for the slow precipitation velocities of the organic compounds or a special chemical is required. They were therefore unable to provide a perfect solution to the problem of deposition of solid matters inside an extraction column.

SUMMARY OF THE INVENTION

A first object of this invention is to provide a stable operation method of a quench column for a reaction product gas containing methacrylic acid, which can prevent the blocking of a nozzle of the quench column and is free from the deposition of high boiling products and tar-like substances in the quench column.

A second object of this invention is to provide a process for preventing the deposition of high boiling products and tar-like substances in a quench column by dividing the quench column into two or more stages and optimizing the temperature of each stage, especially, the temperature of the first stage and the manner of contact between a condensate and a gas.

Further, third and fourth objects of this invention are to provide processes for preventing the formation and deposition of solid matters in a methacrolein diffusion column, in which a condensate is processed further, and in a solvent extraction column for an aqueous solution of methacrylic acid, respectively.

The first object of this invention is achieved by a process for quenching a reaction product gas, which has been obtained by catalytically oxidizing isobutylene, tertiary butanol, methacrolein or isobutyl aldehyde with a molecular oxygen bearing gas in the presence of steam and contains methacrolein and methacrylic acid, with a condensate of the reaction product gas as a cooling medium in a quench column so as to obtain methacrolein and methacrylic acid from the reaction product gas, which comprises:

passing the reaction product gas and a heat-insulating gas through an inner flow passage and an outer flow passage respectively, said inner and outer passages being formed by a double-wall pipe which is constructed of an inner pipe and an outer pipe surrounding the inner pipe and extends through a wall of the quench column;

releasing the reaction product gas from a reaction product gas releasing portion toward the surface of a condensate remaining in a bottom of the quench column;

spraying a portion of the condensate, said portion having been cooled in advance, against the reaction product gas releasing portion; and recirculating another portion of the condensate to a top of the quench column and causing said another portion of the condensate to undergo counter current contact with the reaction product gas by way of a packing of the quench column.

The second object of this invention is attained by a process for quenching the reaction product gas so as to obtain methacrolein and methacrylic acid from the reaction product gas, which comprises:

guiding the reaction product gas to a quench column;

bringing the reaction gas into counter current contact with a liquid mixture of a portion of a condensate of the quench column and a portion of a condensate from a quench column unit composed of at least one quench column in such a way that the temperature of a bottom of the quench column ranges from 50° C. to 70° C.;

guiding an overhead gas from a top of the quench column to the quench column unit; and bringing the overhead gas into counter current contact with a liquid, which has in advance been condensed and accumulated in the quench column unit, in such a way that the temperature of an overhead gas of the quench column unit ranges from 10° C. to 30° C.

The third object of this invention is attained by adding at least one of at least one organic compound, which is selected from aromatic carboxylic acids and aromatic aldehydes, and metal powder to the aqueous solution of methacrylic acid, said aqueous solution having been obtained by quenching the reaction product gas, so that organic compounds, such as terephthalic acid, contained in the aqueous solution are precipitated; and separating and removing the organic compounds thus precipitated.

The fourth object of this invention is achieved by adding at least one of at least one organic compound, which is selected from aromatic carboxylic acids and aromatic aldehydes, and metal powder to an aqueous solution of methacrylic acid, said aqueous solution having been obtained by removing light distillates such as methacrolein from the aqueous methacrylic acid solution obtained by quenching the reaction product gas, so that organic compounds, such as terephthalic acid, contained in the aqueous solution are precipitated; and separating and removing the organic compounds thus precipitated.

DETAILED DESCRIPTION OF THE INVENTION

Figure 1:
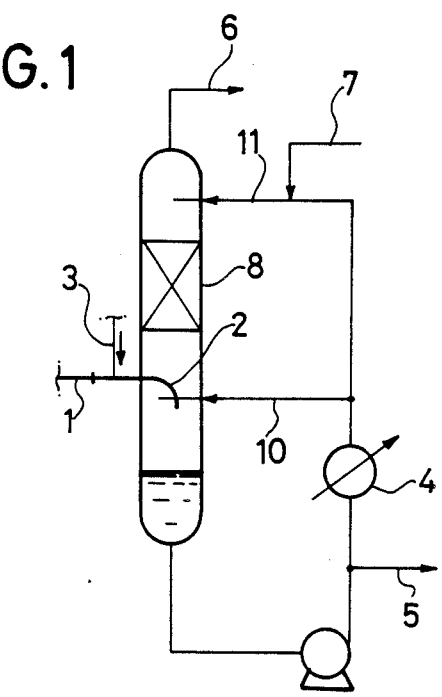
FIG. 1 is a simplified flow diagram of one example of apparatus suitable for use in the practice of the quenching process of this invention.

The reaction product gas containing methacrylic acid, to which the present invention is applied, is obtained by catalytically oxidizing isobutylene, tertiary butanol, methacrolein or isobutyl aldehyde with molecular oxygen in the presence of steam in accordance with a 1-stage or 2-stage reaction Regarding such a reaction, the catalytic reactions disclosed in U.S. Pat. Nos. 4,001,317 and 4,301,031 are known by way of example. The present invention can be applied to a reaction product gas obtained by any one of such catalytic reactions.

As a gas bearing molecular oxygen useful in the practice of this invention, may generally be mentioned air, pure oxygen, or a mixed gas of nitrogen and oxygen. Carbon monoxide, carbon dioxide and the like may also be contained in the gas. The temperature of the reaction product gas may generally be within a range of 230°-370° C. The temperature of the condensate of the quench column may generally be controlled to 10°-100° C., preferably, to 40°-60° C.

The reaction product gas obtained by the above-mentioned reaction contains byproducts, for example, carboxylic acids such as formic acid, acetic acid, propionic acid, maleic acid, citraconic acid, benzoic acid, toluic acid and terephthalic acid and aldehydes such as formaldehyde, acetaldehyde, propionaldehyde, methacrolein, benzaldehyde, tolualdehyde and furfural, in addition to methacrylic acid as the target product.

The heat insulating gas employed for the attainment of the first object of this invention may be preferably such a gas that does not impair the recovery of the reaction product and has heat insulating effects as great as possible. In general, air, nitrogen or a mixed gas of nitrogen and oxygen may be used. The heat insulating gas may contain carbon monoxide, carbon dioxide, etc.

A description will hereinafter be made with reference to FIG. 1. A reaction product gas, which has been obtained by vapor-phase oxidation of isobutylene or the like and has flowed out of a reaction zone (not shown), is introduced into a feed line 2 via a feed line 1. The reaction product gas is fed through the feed line 2 and is then released from a reaction product gas releasing portion of a quench column 8 toward the surface of a condensate remaining in a bottom of the quench column. The condensate cooled by a heat exchanger 4 is fed through a feed line 10 and is sprayed through a sprayer 12 (see FIG. 3), whereby the condensate is brought into parallel flow contact with the reaction product gas released from the reaction product gas releasing portion. A majority of the reaction product gas is quenched adiabatically to substantially the middle temperature between its initial temperature and the temperature of the condensate, so that its condensable components are condensed partly.

Thereafter, the remaining reaction product gas changes its direction and flows upward. In the course of its upward flow, the reaction product gas is brought into counter current contact with the condensate from a top feed line 11 so that the remaining portions of the condensable components are cooled and collected almost completely. Here, the ratio of the condensate portion delivered to the side of the sprayer 12 to that fed to the side of a top of the quench column may preferably range from 1:5 to 1:20.

Figure 2:
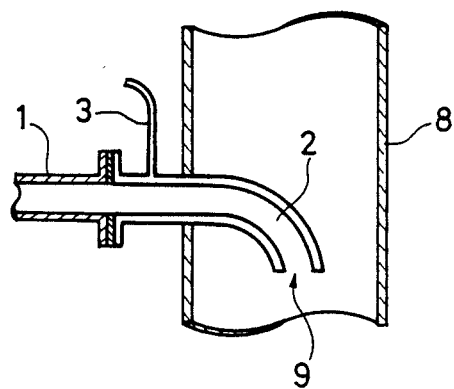
FIGS. 2 and 3 illustrate respectively a reaction gas releasing portion and a condensate spraying portion of a quench column in the exemplary apparatus.

The gas phase containing uncondensed methacrolein and methacrylic acid is guided to the next step through a guide line 6. When the reaction product gas is released into the quenching column as shown in the detailed view of FIG. 2, the insulating gas supplied to an insulating gas blow-out port 9 by way of an insulating gas feed line 3 forms an atmosphere of the insulating gas so that the following merits are brought about. Namely, the quenching spray of the condensate shown in FIG. 3 does not contact the hot feed line 2 directly, thereby preventing the concentration of the condensate, the precipitation of high boiling byproducts, and the polymerization of methacrolein and methacrylic acid. In addition, the feed line 2 is not cooled owing to the effect of the heat insulating gas at its through portion where the feed line 3 extends through a part of a side wall of the quench column 8. Accordingly, the high boiling byproducts do not deposit inside the feed line 2 and its blocking is completely prevented. Here, it is preferable to maintain a flow rate of 0.3–5m/sec for the heat insulating gas which is released from the feed line 3.

Since the reaction product gas is blown against the surface of the condensate in the bottom of the column and the inner wall of the column is completely wet with the condensate owing to the dispersing effects of a packed material, the packed material is not dried locally by the hot reaction product gas which has flowed into the quench column. No blocking phenomenon therefore takes place not only in the feed line 2 but also anywhere in the column. Incidentally, a polymerization inhibitor is fed trough a line 7, while the condensate is drawn out from a guide line 5. The quenching of the reaction product gas is performed while usually maintaining the ratio L/G within a range of 0.3–2.0 in which G is the amount of the reaction gas while L is the amount of the condensate recirculated from the bottom of the column.

A specific process for achieving the above-described second object of the present invention is now described with reference to FIG. 4.

A reaction product gas, which has been obtained by subjecting isobutylene, tertiary butanol, isobutyl aldehyde or methacrolein to a vapor-phase reaction with a molecular oxygen bearing gas in the presence of steam, is introduced into a bottom portion 12 of a first quench column through the feed line 1. A portion of a bottom of the first quench column is drawn out through a line 20, subjected to heat-exchange in a heat-exchanger 14 and recirculated together with a portion of a bottom of a bottom portion 13 of a second quench column, said portion being fed via a line 24, through a line 21, whereby the temperature of the bottom of the first quench column is controlled within 50°–70° C. If the temperature of the bottom of the first quench column becomes lower than 50° C., solid matters formed in the first quench column cannot be collected by these quench columns and remain in the gas in the subsequent steps. Any temperatures higher than 70° C. are not usable because methacrylic acid and the like in the bottom begin to polymerize at such high temperatures. If the bottom of the second quench column is discharged out of the system by way of a line 25 indicated by a dotted line in FIG. 4 and is not recirculated to the first quench column, the bottom drawn from the first quench column via the line 18 has problems in its quality as a liquid such that the concentration of methacrylic acid becomes high, thereby developing inconvenience such as polymerization in the first quench column.

The gas, which has not condensed in the first quench column, is fed to the bottom portion 13 of the second quench column by way of a line 17. It is preferable to control the temperature of gas in the line 17 as close as possible to the temperature of the bottom of the first quench column.

As in the first quench column, a portion of the bottom of the second quench column is recirculated via lines 23, 26 and 27 and is fed through a top portion of the second quench column. The portion of the bottom is cooled to such an extent that a gas flowed out of the top portion has a temperature of 10°–30° C. in a line 22.

If the temperature of the gas flowed out of the top portion of the second quench column is higher than 30° C., the thermal load of the next step, namely, the methacrolein absorption step becomes great. Such a high temperature is therefore disadvantageous industrially. On the other hand, the quantity of heat to be exchanged in the heat exchanger 14 becomes great in order to lower the gas temperature below 10° C. This leads to a problem such that the initial cost for the heat exchanger 15 increases, since the temperature difference between the gas and a cooling medium is small.

In the above description, the quench column unit in this invention was composed of only one quench column. A similar quenching operation is however feasible by a quench column unit constructed of two or more quench columns, preferably, three or more quenching columns. When using such a multi-stage quench column unit, the temperature and flow rate in each stage may be controlled suitably as needed.

Liquids condensed in these quench columns are eventually combined with the bottom of the first quench column, drawn out of the system by way of a line 19, and then fed to the next step, namely, the separation step of methacrolein and methacrylic acid.

A specific process for achieving the above-described third object of this invention will next be described.

According to the aforementioned third process of this invention, organic compounds, such as terephthalic acid, dissolved in a supersaturated state in the aqueous methacrylic acid solution from the line 19 by way of example can be separated at accelerated precipitation velocities by adding at least one of at least one organic compound, which is selected from aromatic carboxylic acids and aromatic aldehydes, and metal powder. In this manner, the organic compounds such as terephthalic acid can be easily separated in the step prior to the diffusion column in which light distillates such as methacrolein are removed, so that their conversion into solids and deposition inside the diffusion column can be avoided and their conversion into solids and deposition in columns in the subsequent steps can also be avoided completely.

The aromatic carboxylic acids and aromatic aldehydes are only sparingly soluble in the aqueous solution of methacrylic acid and may include, for example, aromatic carboxylic acids such as terephthalic acid and isophthalic acid and aromatic aldehydes such as terephthalic aldehyde and isophthalic aldehyde. Since solid matters occurred and separated upon practice of the process are organic compounds composed principally of terephthalic acid, the recycled use of a portion of terephthalic acid separated and recovered may be mentioned as a preferred method.

As the metal powder, stainless steel powder may be mentioned by way of example. Although no particular limitation is imposed on the particle size of metal powder to be used, the preferable particle size ranges from 5 μm to 50 μm.

As a method for adding the organic compound and/or metal powder, it may be thrown directly into a reservoir of the aqueous methacrylic acid solution From the industrial viewpoint, it is however preferable to add it continuously and in a constant proportion relative to the aqueous methacrylic acid solution It is more preferable to add the organic compound and/or metal powder under stirring. Its proportion may range from 100 ppm to 1% by weight based on the aqueous methacrylic acid solution, with a range of 600–6,000 ppm being particularly preferred. Although the organic compounds such as terephthalic acid may be caused to precipitate at normal temperature, it is preferable to conduct the precipitation at a temperature equal to the bottom temperature of the diffusion column upon stripping methacrolein and the like from the aqueous methacrylic acid solution, namely, 50° C. or at a temperature up to about 10° C. lower than the bottom temperature, if feasible.

A further description will next be made with reference to FIG. 5. The aqueous methacrylic acid solution obtained by quenching the reaction product gas is continuously charged into a stirred tank 28 via the line 19. In addition, a portion of a thick slurry with organic compounds, such as terephthalic acid, precipitated as solids therein is recirculated to the line 19 from a solids thickener tank 29, which is to be employed to perform a subsequent step, via a line 30 and is combined.

After the organic compounds, such as terephthalic acid, dissolved in a supersaturated state in the stirred tank 28 are caused to precipitate in the stirred tank 28, the resulting liquid mixture discharged from the stirred tank 28 is guided by a line 31 and the organic compounds such as terephthalic acid are allowed to sediment as solids in the next solids thickener tank 29.

One hour or so is sufficient as the residence time in the stirred tank 28. About one hour is also desirable from the viewpoint of continuous process. An aqueous methacrylic acid solution, from which organic compounds such as terephthalic acid have been removed as solids, is fed as a supernatant solution to an upper portion of a diffusion column 33 via a line 32. Light distillates such as methacrolein are eliminated through a top line 34 of the diffusion column 33, and the resultant aqueous methacrylic acid solution free of light distillates such as methacrolein is discharged as a bottom from a line 35 opening in the bottom of the diffusion column 33.

The capacity of the solids thickener tank 29 may be determined depending on the tolerable quantity range of solids which flow out into the line 32. When the residence time is set at a time as long as 1 hour, substantially no solids are observed to flow out. A filter or the like may however be provided with the line 32 in order to ensure their elimination.

As described above, the thick slurry of the organic compounds such as terephthalic acid, which has been drawn out from the bottom of the solids thickener tank 29, is partly recirculated as a seed slurry for the precipitation of organic compounds dissolved in a supersaturated state in the aqueous methacrylic acid solution from the line 30. In this case, the thick slurry may be recirculated directly to the stirred tank 28 albeit not illustrated in FIG. 5. The remaining portion of the thick slurry is drawn out of the system by way of a line 36. If necessary, the slurry drawn out via the line 36 may be filtered to recover an aqueous solution of methacrylic acid.

Finally, a specific process for attaining the fourth object of this invention is described.

Figure 4:
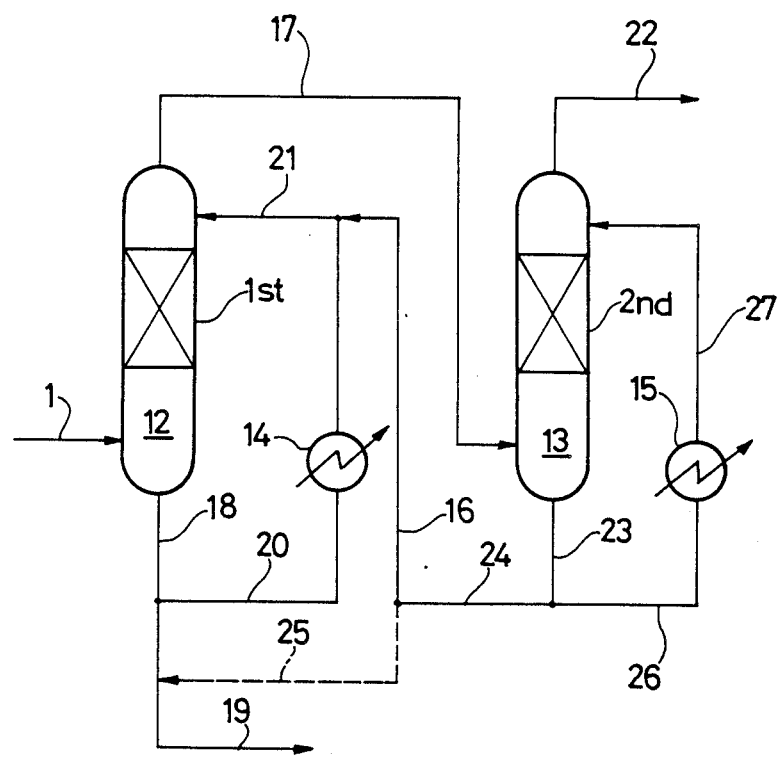
FIG. 4 is a flow diagram of a quenching system useful in the practice of a preferred embodiment of this invention, which comprises a first quench column and a second quench column.

In this embodiment, the above-described organic compound selected from aromatic carboxylic acids and aromatic aldehydes and/or the metal powder is added to the aqueous methacrylic acid solution obtained after the removal of light distillates such as methacrolein and recirculated, for example, through the line 24 shown in FIG. 4, whereby organic compounds, such as terephthalic acid, contained in the aqueous methacrylic acid solution are precipitated and separated. As a result, it is possible to avoid precipitation and deposition of the organic compounds in an extraction column in which extraction of the aqueous methacrylic acid solution with an extracting solvent is to be performed next. Here, the additive may be incorporated in a proportion of 100 ppm—1% based on the aqueous methacrylic acid solution, with a range of 500–4,000 ppm being particularly preferred. Although the organic compounds such as terephthalic acid may be precipitated at room temperature, it is preferable to perform their precipitation within a temperature range of from the temperature of the extraction column upon selective extraction of methacrylic acid to a temperature about 10° C. lower than the aforementioned temperature. One embodiment of practice in this case will next be described with reference to FIG. 5. The flow of this embodiment can be envisaged with ease provided that the diffusion column 33 for light distillates such as methacrolein is read as a solvent extraction column. Namely, the aqueous methacrylic acid solution from which the organic compounds such as terephthalic acid have been precipitated out is fed as a supernatant solution to an upper portion of an extraction column 33 via the line 32. Methacrylic acid is extracted with an extracting solvent 37 fed to a bottom portion of the extraction column 33, although the drawing does not show any feed line for the extracting solvent 37. The resultant extract is allowed to flow out through a top line 34. The extracting solvent added to the aqueous methacrylic acid solution in this process is a solvent capable of selectively extracting methacrylic acid. Illustrative examples of the extracting solvent include heptane, octane, toluene and xylene, and mixtures of two or more of such solvents.

The processes for attaining the first to fourth objects of this invention have been described as a series of steps. Each of the processes can however be practiced separately to bring about its own advantages. Although it is recommended as a more preferable process to practice the first to fourth embodiments of this invention as a series of steps, it is not essential to practice the present invention as such a series of steps.

EXAMPLE 1

In an apparatus for producing methacrylic acid by catalytic vapor-phase oxidation of isobutylene, isobutylene was oxidized into methacrolein in a first-stage oxidation reactor, methacrolein was oxidized into methacrylic acid in a second-stage oxidation reactor, and a reaction product gas flowed out of the second-stage oxidation reactor was blown into a quench column of the type illustrated in FIG. 1.

Through the feed line 1, the reaction product gas consisting of 0.3 mole % of methacrolein, 2.0 mole % of methacrylic acid, 36.0 mole % of water, 61.4 mole % of non-condensable gas and 0.3 mole % of other gas was released at 230° C. and 0.3 kg/cm², which did not allow high boiling gas components to condense or coagulate inside the feed line 1, toward the bottom portion of the quench column 8. On the other hand, air of normal temperature introduced through the feed line 3 was blown out through the annular blow-out port 9 for heat-insulating gas so that the reaction product gas flowed out of the feed line 2 was maintained in an adiabatic state.

In order to operate the quench column at a condensate recirculation rate of 5000 l/hr a condensate temperature of 50°-60° C. and an overhead gas temperature of 41° C., a condensate was cooled in the heat exchanger 4 and was sprayed at 4000 l/hr from the top of the quench column and at 1000 l/hr against a reaction product gas releasing portion. A liquid thus condensed and increased was drawn out by a liquid level controller and was fed to the next step via the guide line 5, while the gaseous phase was supplied to the next step by way of the guide line 6.

In the above operation, no pressure increase was observed in the system over 6 months. After stopping the operation, the reaction product gas line and the inside of the quench column were inspected. Absolutely no changes were observed except for the occurrence of a thin deposit of a black substance at the reaction product gas releasing portion.

COMPARATIVE EXAMPLE 1

Figure 3:
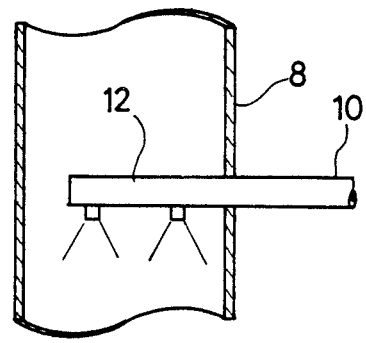

In an apparatus for producing methacrylic acid by catalytic vapor-phase oxidation of isobutylene, isobutylene was oxidized into methacrolein in a first-stage oxidation reactor, methacrolein was oxidation into methacrylic acid in a second-stage oxidization reactor, and a reaction product gas flowed out of the second-stage oxidation reactor was blown into a quench column of the type illustrated in FIG. 3 of Japanese Patent Laid-Open No. 91944/1982.

Through a feed line, the reaction product gas consisting of 0.3 mole % of methacrolein, 2.0 mole % of methacrylic acid, 36.0 mole % of water, 61.4 mole % of non-condensable gas and 0.3 mole % of other gas was released at 230° C. and 0.3 kg/cm², which did not allow high boiling gas components to condense or coagulate inside the feed line, through a nozzle provided at a top portion of the quench column Through another feed line, air heated to 230° C. was blown at an average gas flow velocity of 100 m/sec to the periphery of the nozzle.

In order to operate the quench column under an item consisting of a condensate recirculation rate of 10 ton/hr, a condensate temperature of 50-60° C. and a discharge gas temperature of 41° C., a condensate was cooled in a heat exchanger and was sprayed as a parallel flow from the top of the quench column. Incidentally, a polymerization inhibitor was also charged into a condensate recirculation line and sprayed downwardly from the top of the quench column. A liquid thus condensed and increased was drawn out by a liquid level controller provided at a bottom portion of the quench column, while a gaseous phase was drawn out at a point above the surface of the condensate and supplied to the next step. Although no pressure increase was observed and the operation remained good even 30 days after the initiation of the operation, a gradual pressure increase was observed after the beginning of the second month. The operation was therefore stopped and the inside of the quench column was inspected. Black tar-like substances were found to have deposited and grown on the inner wall of the column in the vicinity of the recirculation line for the condensate, so that the flow passage in the column was reduced.

EXAMPLE 2

After a reaction product gas, which had been obtained by subjecting methacrolein to vapor-phase catalytic oxidation in the presence of air and steam while using an oxidation catalyst of the heteropoly-acid type, was cooled to about 260° C. in an indirect cooler, an experiment was conducted by using facilities having equipment similar to those shown in FIG. 4 and described in Table 1. The operation was conducted to control the temperature of the bottom of the bottom portion 12 of the first quench column at about 58° C. and the temperature of the gas from the line 22 of the second quench column at about 11° C. When the flow rate and composition in each line became steady, the flow rate, temperature and composition were determined. Results are shown in Table 2. After the determination, it was possible to conduct a continuous operation over about 2,000 hours without troubles. After stopping the reaction, the first and second quench columns, the other equipment, the lines 17, 22 and the like were inspected internally. Deposition of solid matters such as polymerized substances and terephthalic acid was not observed.

TABLE 1

|  | 1st Quench column | 2nd Quench column |
|---|---|---|
| Type | Packed column | Packed column |
| Column diameter | 10B | 8B |
| Height | Packed 3 m high | Packed 2 m high |
| Material | SUS316L | SUS316L |
| Packing | ⅜B Paul rings | ⅜B Paul rings |

TABLE 2

| Line No. | 1 | 17 | 19 | 21 | 22 | 1 | 27 |
|---|---|---|---|---|---|---|---|
| Total flow rate (kg/hr) | — | — | 38.2 | 5000.0 | — | — | 800.0 |
| Temperature (°C.) | 263.5 | 53.5 | 57.4 | 54.7 | 11.2 | 13.5 | 11.8 |
| GS* (kg/hr) | 140.5 | 140.5 | — | — | 140.5 | — | — |
| $H_2O$ (kg/hr) | — | — | 15.6 | — | — | — | — |
| Methacrylic acid (kg/hr) | 9.7 | 0.5 | 9.6 | — | 0.0 | 0.5 | — |
| Methacrolein (kg/hr) | 3.2 | 3.1 | 0.1 | — | — | — | — |
| Solid matters** (kg/hr) | 28.0 | 5.0 | 27.7 | — | 0.3 | — | — |

TABLE 2-continued

| Line No. | 1 | 17 | 19 | 21 | 22 | 1 | 27 |
|---|---|---|---|---|---|---|---|
| Others (kg/hr) | 24.3 | — | 12.2 | — | — | — | — |

*"GS" means the total weight of $N_2$, $O_2$, CO, $CO_2$ and Ar.
**"Solid matters" indicates insoluble matters in the process lines, led by terephthalic acid.
Dash (—) indicates "not measured".

EXAMPLE 3

An experiment was conducted in exactly the same manner as in Example 2 except temperature conditions described below. As a result, absolutely no problem was observed like Example 2.

Temperature of the overhead gas (line 17) from the first quench column—65.8° C.

Temperature of the bottom (line 19) of the first quench column—69.7° C.

Other conditions were as in Example 2.

COMPARATIVE EXAMPLE 2

The first quench column was operated in exactly the same manner as in Example 2 while controlling the temperature of the first quench column in such a way that the temperature of the bottom was 38° C. and the temperature of the gas (line 17) at the top was 34° C. The same temperature conditions were applied to the second quench column. The weights of solid matters such as terephthalic acid in the lines 17 and 22 were 15 g/hr and 10 g/hr respectively. In about 700 hours after the initiation of the operation, the blocking of the first quench column progressed and the condensate flowed out together with the gas through the top of the quench column.

COMPARATIVE EXAMPLE 3

In the same facilities as in Example 2, the condensate was caused to flow through the line 25 instead of allowing it to pass through the line 16. In about 20 hours, the first quench column was blocked and its operation was infeasible. At that time, the temperature of the bottom of the first quench column was 62° C. and the concentration of methacrylic acid in the solution was 47.1 wt. %.

COMPARATIVE EXAMPLE 4

In exactly the same manner as in Example 2, the first quench column was operated to give a bottom temperature of 84° C. and a top gas (line 17) temperature of 79° C. The second quench column was operated under the same temperature conditions. The first quench column was blocked by a continuous operation for about 72 hours, so that no further operation was feasible.

EXAMPLE 4

After a reaction product gas, which had been obtained by subjecting methacrolein to vapor-phase catalytic oxidation in the presence of air and steam while using an oxidation catalyst of the heteropoly-acid type, was cooled to about 260° C. in an indirect cooler, the reaction product gas was introduced into a quench column.

The quench column had a diameter of 10 inches and a height of 4 m, and was packed with ⅜B Paul rings over 3 m of its height. A portion of a condensed liquid was fed from a top portion of the column and brought into counter current contact with the reaction product gas. The resultant aqueous solution of methacrylic acid consisted of 30.9 wt. % of methacrylic acid, 540 ppm of dissolved terephthalic acid, 9.5 wt. % of other organic acids and aldehydes, and the remainder of water.

When 1 g of terephthalic acid was added to 1000 g of the aqueous solution, the concentration of organic compounds, such as terephthalic acid dissolved in supersaturation reached equilibrium of 300 ppm in a period as short as 45 minutes.

EXAMPLE 5

When 1 g of stainless powder was added to 1000 g of the aqueous solution of methacrylic acid in Example 4, the concentration of dissolved organic compounds such as terephthalic acid reached equilibrium in 50 minutes.

EXAMPLE 6

Figure 5:
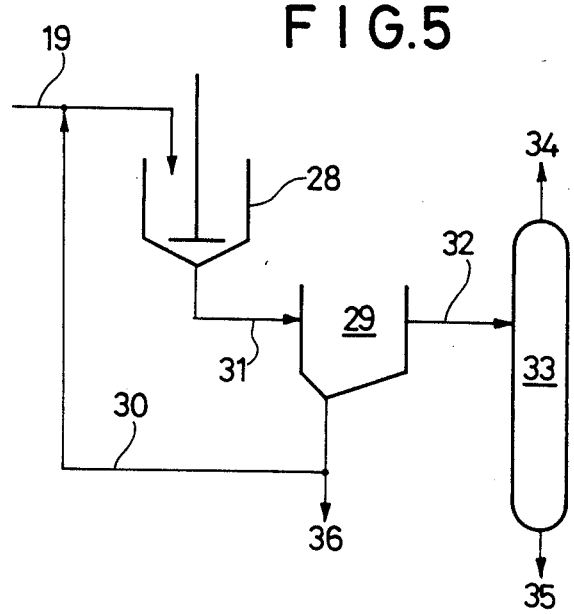
FIG. 5 is a flow diagram of a solids separation system useful in the practice of a preferred embodiment of this invention, which includes a stirred tank and a solids thickener tank.

Using an aqueous methacrylic acid solution similar to that obtained in Example 4, the production of methacrylic acid was conducted by facilities having equipment similar to those shown in the flow of FIG. 5 (the outline of said facilities being given in Table 3).

The aqueous methacrylic acid solution was continuously fed at 30.0 kg/hr to the stirred tank 28. When the entire system reached equilibrium, the flow rate and composition in each line were determined. Results are shown in Table 4. No solid matters were observed in the aqueous methacrylic acid solution in the line 32, which was to be fed to the diffusion column 33 The diffusion column packed with "THRU-THE-PACK BX" over 2.4 m of its height No deposit was observed in the column even when the column was operated for about 2 months at a bottom temperature of 50° C.

TABLE 3

| | Type | Size | Material | Remarks |
|---|---|---|---|---|
| Stirred tank | Axial flow | 14B × 0.4 m | SUS-316 | |
| Solids thickener tank | Horizontal flow | Floor area: 0.3 m$^2$ Height: 0.5 m | SUS-316 | |
| Diffusion column | Packed | 4B × 7.0 m | SUS-316L | "THRU-THE-PACK BX" Packed 2.4 m |

TABLE 4

| Line No. Unit | Flow rate kg/hr | Methacrylic acid wt. % | Organic compounds such as terephthalic acid | | Water wt. % | Others wt. % |
|---|---|---|---|---|---|---|
| | | | Dissolved ppm | Solids ppm | | |
| SAMAS* | 30.0 | 31.0 | 540 | 0 | 59.4 | 9.5 |
| 19 | 31.0 | 30.9 | 530 | 2200 | 59.3 | 9.5 |
| 31 | 31.0 | 30.9 | 320 | 2410 | 59.3 | 9.5 |
| 32 | 30.0 | 31.0 | 320 | 0 | 59.5 | 9.5 |
| 35 | 29.6 | 31.5 | 320 | 0 | 60.0 | 8.5 |
| 30 | 1.0 | 28.9 | 320 | 6.8 | 55.4 | 8.9 |

*SAMAS: Starting aqueous methacrylic acid solution.

EXAMPLE 7

After a reaction product gas, which had been obtained by subjecting methacrolein to vapor-phase catalytic oxidation in the presence of air and steam while using an oxidation catalyst of the heteropoly-acid type, was cooled to about 260° C. in an indirect cooler, the reaction product gas was introduced into a quench column.

The quench column had a diameter of 10 inches and a height of 4 m, and was packed with ⅜B Paul rings over 3 m of its height. A portion of a condensed liquid was fed from a top portion of the column and brought into counter current contact with the reaction product gas. The resultant condensate was fed to a diffusion column, in which light distillates such as methacrolein and acetone were removed under reduced pressure of 300 mmHg abs. An aqueous solution of methacrylic acid was hence obtained from a bottom portion of the column. The thus-obtained aqueous methacrylic acid solution consisted of 31.5 wt. % of methacrylic acid, 530 ppm of dissolved organic compounds such as terephthalic acid, 9.1 wt. % of other organic acids and aldehydes, and the remainder of water.

When 1 g of terephthalic acid was added to 1000 g of the aqueous solution, the concentration of organic compounds, such as terephthalic acid, dissolved in supersaturation dropped and reached equilibrium of 250 ppm in a period as short as 40 minutes.

EXAMPLE 8

When 1 g of stainless powder was added to 1000 g of the aqueous solution of methacrylic acid in Example 7, the concentration of dissolved organic compounds such as terephthalic acid reached equilibrium in 45 minutes.

EXAMPLE 9

Using an aqueous methacrylic acid solution similar to that obtained in Example 7, the production of methacrylic acid was conducted by facilities having equipment similar to those shown in the flow of FIG. 5 except for the replacement of the diffusion column 33 by a rotary disk type extraction column having a diameter of 6 inches and a height of 7 m (the outline of said facilities being given in Table 5).

The aqueous methacrylic acid solution was continuously fed at 30.0 kg/hr to the stirred tank 28. When the entire system reached equilibrium, the flow rate and composition in each line were determined. Results are shown in Table 6. No solid matters were observed in the aqueous methacrylic acid solution in the line 32, which was to be fed to the extraction column. No deposit was observed in the column even when the column was operated for about 2 months at a temperature of 30° C.

TABLE 5

| | Type | Size | Material | Remarks |
|---|---|---|---|---|
| Stirred tank | Axial flow | 14B × 0.4 m | SUS-316 | |
| Solids thickener tank | Horizontal flow | Floor area: 0.3 m² Height: 0.5 m | SUS-316 | |
| Extraction column | Rotary disk | 6B × 7 m | SUS-316L | 70 stages |

TABLE 6

| Line No. Unit | Flow rate kg/hr | Methacrylic acid wt. % | Organic compounds such as terephthalic acid | | Water wt. % | Others wt. % | n-Heptane wt. % |
|---|---|---|---|---|---|---|---|
| | | | Dissolved ppm | Solids ppm | | | |
| SAMAS* | 30.0 | 31.5 | 530 | 0 | 59.4 | 9.1 | — |
| 19 | 31.0 | 31.4 | 520 | 1650 | 59.3 | 9.1 | — |
| 31 | 31.0 | 31.4 | 310 | 1860 | 59.3 | 9.1 | — |
| 32 | 30.0 | 31.5 | 310 | 0 | 59.4 | 9.1 | — |
| 37 | 30.0 | 0 | — | — | 0.0 | 0.1 | 99.9 |
| 34 | 40.3 | 23.5 | 30 | 0 | 0.0 | 2.1 | 74.4 |
| 36 | 1.0 | 29.9 | 290 | 5.1(wt. %) | 55.2 | 9.8 | 0.0 |

*SAMAS: Starting aqueous methacrylic acid solution.

What is claimed is:

1. A process for quenching a reaction product gas, which has been obtained by catalytically oxidizing isobutylene, tertiary butanol, methacrolein or isobutyl aldehyde with a molecular oxygen bearing gas in the presence of steam and contains methacrolein and methacrylic acid, with a condensate of the reaction product gas as a cooling medium in a quench column so as to obtain methacrolein and methacrylic acid from the reaction product gas, which comprises:

passing the reaction product gas and a heat-insulating gas through an inner flow passage and an outer flow passage respectively, said inner and outer passages being formed by a double-wall pipe which is constructed of an inner pipe and an outer pipe surrounding the inner pipe and extends through a wall of the quench column;

releasing the reaction product gas from a reaction product gas releasing portion of the quench column toward the surface of a condensate remaining in a bottom of the quench column;

spraying a portion of the condensate, said portion having been cooled in advance, against the reaction product gas released from the reaction product gas releasing portion of the quench column and recirculating another portion of the condensate to a top of the quench column and causing said another portion of the condensate to undergo counter current contact with the reaction product gas by way of a packing of the quench column.

2. A process for quenching a reaction product gas, which has been obtained by catalytically oxidizing isobutylene, tertiary butanol, methacrolein or isobutyl aldehyde with a molecular oxygen bearing gas in the presence of steam and contains methacrolein and methacrylic acid, so as to obtain methacrolein and methacrylic acid from the reaction product gas, which comprises:

guiding the reaction product gas to a quench column;

bringing the reaction gas into counter current contact with a liquid mixture of a portion of a condensate of the quench column and a portion of a condensate from a quench column unit composed of at least one quench column in such a way that the temperature of a bottom of the quench column ranges from 50° C. to 70° C.;

guiding an overhead gas from a top of the quench column to the quench column unit; and bringing the overhead gas into counter current contact with a liquid, which has in advance been condensed and accumulated in the quench column unit, in such a way that the temperature of an overhead gas of the quench column unit ranges from 10° C. to 30° C.

3. A process for treating an aqueous solution of methacrylic acid so as to obtain methacrolein and methacrylic acid, said aqueous solution having been obtained by quenching a reaction gas resulting from catalytic oxidation of isobutylene, tertiary butanol, methacrolein or isobutyl aldehyde with a molecular oxygen bearing gas in the presence of steam, which comprises:

passing the reaction product gas and a heat-insulating gas through an inner flow passage and an outer flow passage respectively, said inner and outer passages being formed by a double-wall pipe which is constructed of an inner pipe and an outer pipe surrounding the inner pipe and extends through a wall of a quench column, releasing the reaction product gas from a reaction product gas releasing portion of the quench column toward the surface of a condensate remaining in a bottom of the quench column, spraying a portion of the condensate, said portion having been cooled in advance, against the reaction product gas released from the reaction product gas releasing portion of the quench column, and recirculating another portion of the condensate together with a portion of a condensate from a quench column unit composed of at least one quench column to a top of the quench column;

bringing the reaction gas into counter current contact with a liquid mixture of the portion of the condensate from the quench column and the portion of the condensate from the quench column unit by way of a packing of the quench column in such a way that the temperature of a bottom of the quench column ranges from 50° C. to 70° C., guiding an overhead gas from a top of the quench column to the quench column unit, and bringing the overhead gas into counter current contact with a liquid, which has in advance been condensed and accumulated in the quench column unit, in such a way that the temperature of an overhead gas of the quench column unit ranges from 10° C. to 30° C.; and adding at least one of stainless powder and terephthalic acid which has been separated and recovered from the aqueous solution of methacrylic acid to the resultant aqueous solution of methacrylic acid so as to precipitate organic compounds contained in the aqueous solution, and then separating and removing the organic compounds thus precipitated.

4. The process as claimed in claim 3, wherein said at least one of stainless steel powder and said terephthalic acid is added after removing light distillates from the aqueous solution.

* * * * *